(12) United States Patent
Hayama

(10) Patent No.: US 9,759,855 B2
(45) Date of Patent: Sep. 12, 2017

(54) HYBRID NANOPARTICLES AND ILLUMINATION DEVICES USING THE HYBRID NANOPARTICLES

(71) Applicant: Empire Technology Development LLC, Wilmington, DE (US)

(72) Inventor: Hidekazu Hayama, Osaka (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/769,285

(22) PCT Filed: Feb. 25, 2013

(86) PCT No.: PCT/US2013/027660
§ 371 (c)(1),
(2) Date: Aug. 20, 2015

(87) PCT Pub. No.: WO2014/130051
PCT Pub. Date: Aug. 28, 2014

(65) Prior Publication Data
US 2016/0004003 A1 Jan. 7, 2016

(51) Int. Cl.
| | |
|---|---|
| *F21V 8/00* | (2006.01) |
| *C07F 15/00* | (2006.01) |
| *C07F 7/02* | (2006.01) |
| *C09K 11/02* | (2006.01) |
| *C09K 11/06* | (2006.01) |
| *G02F 1/1335* | (2006.01) |

(52) U.S. Cl.
CPC .............. *G02B 6/0065* (2013.01); *C07F 7/02* (2013.01); *C07F 15/0033* (2013.01); *C09K 11/02* (2013.01); *C09K 11/025* (2013.01); *C09K 11/06* (2013.01); *G02B 6/0035* (2013.01); *G02B 6/0041* (2013.01); *C09K 2211/1088* (2013.01); *G02B 6/0055* (2013.01); *G02F 2001/133614* (2013.01)

(58) Field of Classification Search
CPC ......... C07F 7/02; C07F 15/0033; C09K 11/02
See application file for complete search history.

(56) References Cited

U.S. PATENT DOCUMENTS

| | | | |
|---|---|---|---|
| 7,560,859 B2 | 7/2009 | Saito et al. | |
| 2004/0256974 A1* | 12/2004 | Mueller-Mach ... | C09K 11/7774 313/485 |
| 2007/0262302 A1 | 11/2007 | Mochizuki et al. | |

(Continued)

FOREIGN PATENT DOCUMENTS

EP 1566426 A2 8/2005

OTHER PUBLICATIONS

"Acrylic resin", From Wikipedia, accessed at http://en.wikipedia.org/wiki/Acrylic_resin, para 3, p. 1, Mar. 18, 2015.

(Continued)

*Primary Examiner* — Elmito Breval
(74) *Attorney, Agent, or Firm* — Turk IP Law, LLC

(57) ABSTRACT

Hybrid nanoparticles and transparent light guides using the hybrid nanoparticles are disclosed. In some examples, a hybrid nanoparticle may include an organic blue-light emitting material, and an inorganic material bonded to the organic blue-light emitting material.

20 Claims, 9 Drawing Sheets

(56) References Cited

U.S. PATENT DOCUMENTS

| | | |
|---|---|---|
| 2008/0198300 A1 | 8/2008 | Okumura et al. |
| 2011/0068321 A1 | 3/2011 | Pickett et al. |
| 2011/0241229 A1 | 10/2011 | Naasani et al. |
| 2012/0223273 A1 | 9/2012 | Wiesner et al. |
| 2012/0223341 A1 | 9/2012 | Yamamoto et al. |

OTHER PUBLICATIONS

Bolink, H.J., et al., "Origin of the large spectral shift in electroluminescence in a blue light emitting cationic iridium (III) complex," Journal of Materials Chemistry, vol. 17, Issue 48, pp. 5032-5041 (Nov. 5, 2007).

Chen, E-C., et al., "Infrared proximity sensor using organic light-emitting diode with quantum dots converter," Organic Electronics, vol. 13, Issue 11, pp. 2312-2318 (Nov. 2012).

Handl, H.L., and Gillies, R.J., "Lanthanide-based luminescent assays for ligand-receptor interactions," Life sciences, vol. 77, No. 4, pp. 361-371 (Jun. 10, 2005).

International Search Report and Written Opinion for International Application No. PCT/US2013/27660 mailed Apr. 30, 2013.

Thangthong, A-M., et al., "Synthesis and characterization of 9,10-substituted anthracene derivatives as blue light-emitting and hole-transporting materials for electroluminescent devices," Tetrahedron, vol. 68, Issue 7, pp. 1853-1861 (Feb. 18, 2012).

Xu, Y., et al., "Sol-gel broadband anti-reflective single-layer silica films with high laser damage threshold," Thin Solid Films, vol. 440, Issue 1-2, pp. 180-183 (Sep. 1, 2003).

* cited by examiner

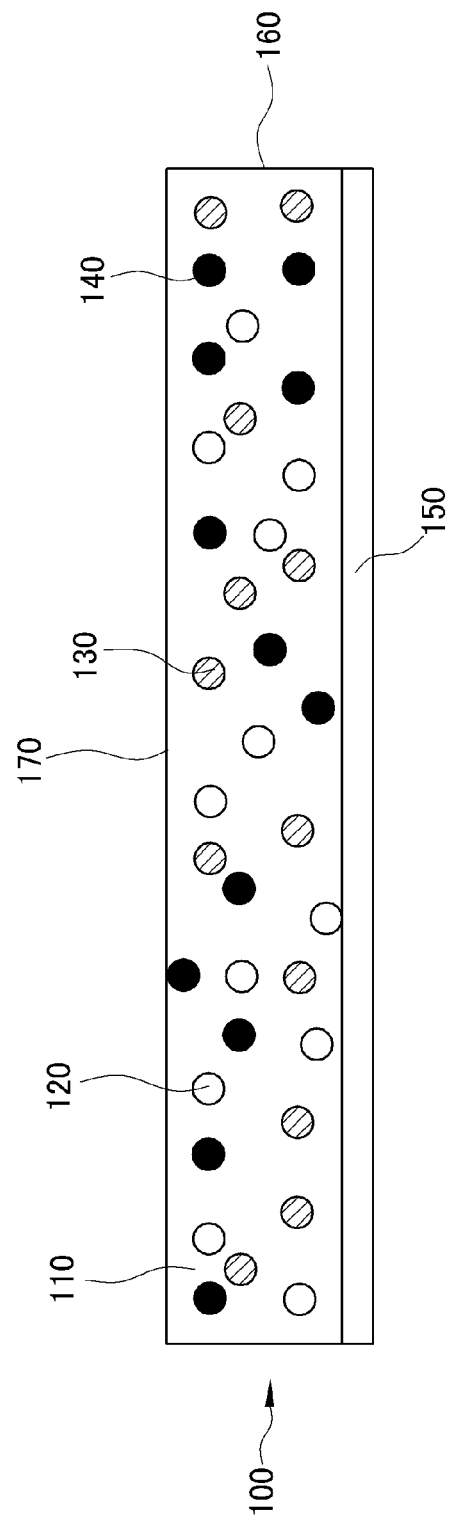

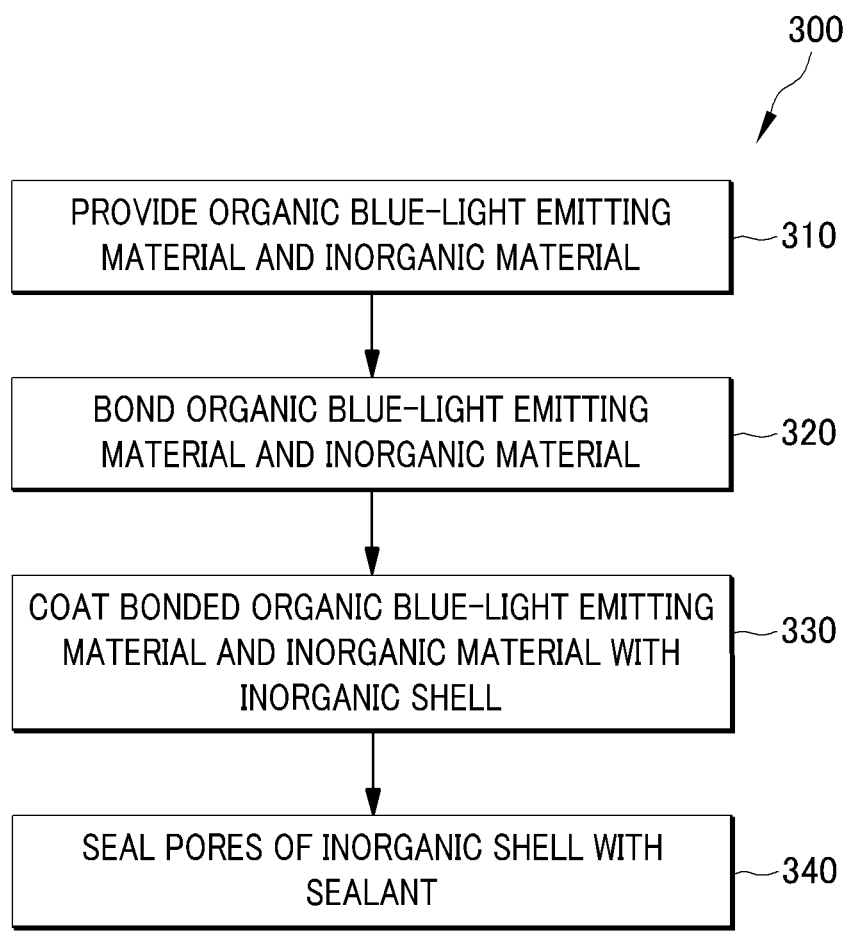

the claims in the present application are not prior art to
HYBRID NANOPARTICLES AND ILLUMINATION DEVICES USING THE HYBRID NANOPARTICLES

CROSS-REFERENCE TO RELATED APPLICATION

This application is the U.S. National Phase under 35 U.S.C. §371 of International Application No. PCT/US2013/027660, filed on Feb. 25, 2013, the entire contents of which is herein incorporated by reference.

BACKGROUND

Unless otherwise indicated herein, the materials described herein are not prior art to the claims in the present application and are not admitted to be prior art by inclusion in this section.

A liquid crystal display (LCD) is a flat panel display which uses light modulating properties of liquid crystals. Since the liquid crystals do not emit light themselves, the LCD generally employs backlight illumination. For the LCD backlight, or for other planar illumination devices, a light emitting device, such as a light emitting diode (LED), and a transparent light guide for guiding and diffusing the light from the light emitting device can be used.

SUMMARY

Some embodiments disclosed herein include a hybrid nanoparticle including an organic blue-light emitting material, and an inorganic material bonded to the organic blue-light emitting material. In some embodiments, the organic blue-light emitting material may include at least one of a blue fluorescent material and a blue phosphorescent material. By way of example, but not limitation, the blue fluorescent material may include at least one of 9,10-dibromoanthracene, a bis-(triazinylamino)stilbenedisulfonic acid derivative, a bis-stilbiphenyl derivative, and 2,5-bis(5-tert-butyl-2-benzoxazolyl)thiophene; and the blue phosphorescent material may include an iridium(III) complex including at least one of tris(2-(2,4-difluorophenyl)pyridinate)iridium(III), bis(2-(2,4-difluorophenyl)pyridinate)picolinic acid iridium(III), tris(3,4,7,8-tetramethyl-1,10-phenantrolinato)iridium(III), and tris(2,9-dimethyl-4,7-diphenyl-1,10-phenanthrolinato)iridium(III). By way of example, but not limitation, the inorganic material may include silica.

In some embodiments, the inorganic material may be physically bonded to the organic blue-light emitting material. In some embodiments, the inorganic material may be covalently bonded to the organic blue-light emitting material. In some embodiments, the inorganic material may be hydrogen-bonded to a resin containing the organic blue-light emitting material. By way of example, but not limitation, the resin may include a polyvinylpyrrolidone (PVP) resin.

In some embodiments, the hybrid nanoparticle may further include an inorganic shell encapsulating the organic blue-light emitting material and the inorganic material bonded to each other. In some embodiments, the inorganic shell may include a silica shell. In some embodiments, the inorganic shell may have pores, and the pores may be sealed with at least one of a transition metal salt (e.g., a salt of iron, cobalt, nickel, or copper, etc.), a transition metal complex salt (e.g., a complex salt of iron, cobalt, nickel, or copper, etc.), and a transition metal chloride (e.g., a chloride of iron, cobalt, nickel, or copper, etc.).

Alternative embodiments disclosed herein may include a transparent light guide including a resin containing at least one red-light emitting material, at least one green-light emitting material, and at least one organic blue-light emitting material bonded with an inorganic material; and a reflecting sheet. In some embodiments, the reflecting sheet may be disposed to cover one side of surface of the resin.

By way of example, but not limitation, the resin may include an acrylic resin. By way of example, but not limitation, the red-light emitting material may include a $Eu^{3+}$ tri-n-butyl complex. In some embodiments, the green-light emitting material may include a $Tb^{3+}$ tri-n-butyl complex. By way of example, but not limitation, the organic blue-light emitting material may include at least one of a blue fluorescent material including 9,10-dibromoanthracene, a bis-(triazinylamino)stilbenedisulfonic acid derivative, a bis-stilbiphenyl derivative, and 2,5-bis(5-tert-butyl-2-benzoxazolyl)thiophene; and a blue phosphorescent material including tris(2-(2,4-difluorophenyl)pyridinate)iridium(III), bis(2-(2,4-difluorophenyl)pyridinate)picolinic acid iridium(III), tris(3,4,7,8-tetramethyl-1,10-phenantrolinato)iridium(III), and tris(2,9-dimethyl-4,7-diphenyl-1,10-phenanthrolinato)iridium(III). By way of example, but not limitation, the inorganic material may include silica.

In some embodiments, the organic blue-light emitting material bonded with the inorganic material may be coated with silica. In some embodiments, a surface of the organic blue-light emitting material bonded with the inorganic material may be sealed with at least one of a transition metal salt, a transition metal complex salt, and a transition metal chloride.

Also provided is a backlight for a liquid crystal display including any of the transparent light guides provided herein.

Also provided is a planar illumination device including any of the transparent light guides provided herein.

Yet alternative embodiments disclosed herein may include a method of forming a hybrid nanoparticle. The method may include providing an organic blue-light emitting material, and bonding an inorganic material to the organic blue-light emitting material to form a hybrid nanoparticle.

In some embodiments, the bonding step may include bonding the inorganic material to the organic blue-light emitting material physically.

In some embodiments, the bonding step may include preparing a compound of the organic blue-light emitting material and an alkoxy group, and hydrolysis-condensing the alkoxy group with an alkoxysilane. By way of example, but not limitation, the alkoxy group may be an ethoxy group, and the alkoxysilane may be tetraethoxysilane (TEOS).

In some embodiments, the bonding step may include pi-electron-conjugating the organic blue-light emitting material and a silane coupling agent containing an alkoxy group, and hydrolysis-condensing the alkoxy group with an alkoxysilane. By way of example, but not limitation, the silane coupling agent may include phenyltriethoxysilane, the alkoxy group may include an ethoxy group, and the alkoxysilane may include tetraethoxysilane (TEOS).

In some embodiments, the bonding step may include mixing the organic blue-light emitting material with a resin, and forming a hydrogen-bond between the resin and the inorganic material. By way of example, but not limitation, the resin may include a polyvinylpyrrolidone (PVP) resin.

In some embodiments, the method may further include coating the hybrid nanoparticle with an inorganic shell. By way of example, but not limitation, the inorganic shell may include a silica shell. In some embodiments, the method may further include sealing pores of the inorganic shell with at least one of a transition metal salt, a transition metal complex salt, and a transition metal chloride. In some embodiments, the method may further include sealing pores of the hybrid nanoparticle with at least one of a transition metal salt, a transition metal complex salt, and a transition metal chloride.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1 schematically shows an illustrative example of a transparent light guide, arranged in accordance with at least some embodiments described herein;

FIG. 3 illustrates an example flow diagram of a process for forming a hybrid nanoparticle, arranged in accordance with at least some embodiments described herein;

DETAILED DESCRIPTION

Figure 2A:
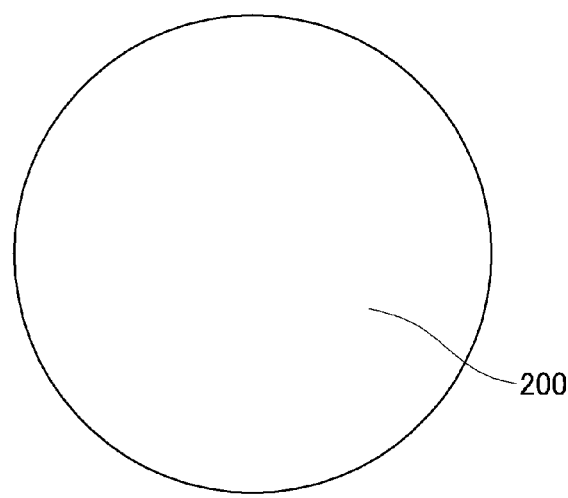
FIGS. 2A-2D schematically show illustrative examples of hybrid nanoparticles, arranged in accordance with at least some embodiments described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the drawings, can be arranged, substituted, combined, separated, and designed in a wide variety of different configurations, all of which are explicitly contemplated herein.

Technologies are herein generally described for hybrid nanoparticles and transparent light guides using the hybrid nanoparticles.

In some examples, a transparent light guide may include a transparent resin uniformly containing at least one red-light emitting material, at least one green-light emitting material, and at least one blue-light emitting material; and a reflecting sheet disposed to cover one side of surface of the resin. A light source disposed adjacent to the transparent light guide may emit light, and the light emitted by the light source may be incident on a side end face of the resin. The light entered into the resin may excite the at least one red-light emitting material, at least one green-light emitting material, and at least one blue-light emitting material, thereby generating white-light. The transparent light guide may emit the generated white-light from the other side of surface of the resin, i.e., the surface where the reflecting sheet is not disposed.

In some examples, the light source may be an ultraviolet light emitting diode (UV-LED) configured to generate and emit ultraviolet light; and the red-light emitting material may include a $Eu^{3+}$ tri-n-butyl complex configured to emit red-light when excited by ultraviolet light, the green-light emitting material may include a $Tb^{3+}$ tri-n-butyl complex configured to emit green-light when excited by ultraviolet light, and the blue-light emitting material may include an organic blue-light emitting material such as a blue fluorescent material and/or a blue phosphorescent material configured to emit blue-light when excited by ultraviolet light. To improve durability of the organic blue-light emitting material against the ultraviolet light, a hybrid nanoparticle including the organic blue-light emitting material and an inorganic material may be used as the blue-light emitting material. The organic blue-light emitting material and the inorganic material may be bonded to each other, e.g., physically, covalently, or via hydrogen-bonding.

FIG. 1 schematically shows an illustrative example of a transparent light guide 100, arranged in accordance with at least some embodiments described herein.

As depicted, transparent light guide 100 may include a resin 110, which may uniformly contain at least one red-light emitting material 120, at least one green-light emitting material 130, and at least one blue-light emitting material 140. In some embodiments, blue-light emitting material 140 may be a hybrid nanoparticle including at least one organic blue-light emitting material and at least one inorganic material. In some embodiments, red-light emitting material 120, green-light emitting material 130 and blue-light emitting material 140 may be uniformly distributed in resin 110 by mixing and/or stirring red-light emitting material 120, green-light emitting material 130, blue-light emitting material 140, a monomer of resin 110 (e.g., methyl methacrylate, etc.), and at least one thermal polymerization initiator (e.g., benzoyl peroxide, etc.); casting the mixture between two plates that are not penetrated by the monomer (e.g., glass plates, metal plates, teflon plates, etc.); and curing the mixture casted between the two plates.

In some embodiments, transparent light guide 100 may further include a reflecting sheet 150, which may be disposed to cover one side of surface of resin 110. In some embodiments, reflecting sheet 150 may be adhered to the surface of resin 110 by an adhesive, or reflecting sheet 150 may be formed on the surface of resin 110 by applying an ink with light scattering properties (e.g., an ink containing titanium oxide fillers).

In some embodiments, light emitted from a light source (e.g., UV-LED) (not shown) may be incident on a side end face 160 of resin 110, and may excite red-light emitting material 120, green-light emitting material 130 and blue-light emitting material 140 contained in resin 110. The excited red-light emitting material 120, green-light emitting material 130 and blue-light emitting material 140 may respectively generate red-light, green-light and blue-light, and the generated red-light, green-light and blue-light may be mixed to generate white-light. Then, transparent light guide 100 may emit the generated white-light from a surface 170 of resin 110.

By way of example, but not limitation, resin 110 may be a transparent resin such as an acrylic resin. By way of example, but not limitation, red-light emitting material 120 may include a $Eu^{3+}$ tri-n-butyl complex. By way of example, but not limitation, green-light emitting material 130 may include a $Tb^{3+}$ tri-n-butyl complex. By way of example, but not limitation, the organic blue-light emitting material in blue-light emitting material 140 may include a blue fluorescent material including 9,10-dibromoanthracene, a bis-(triazinylamino)stilbenedisulfonic acid derivative, a bis-stilbiphenyl derivative, and 2,5-bis(5-tert-butyl-2-benzoxazolyl)thiophene, etc.; and/or a blue phosphorescent material including tris(2-(2,4-difluorophenyl)pyridinate)iridium(III), bis(2-(2,4-difluorophenyl)pyridinate)picolinic acid iridium(III), tris(3,4,7,8-tetramethyl-1,10-phenantrolinato)iridium(III), and tris(2,9-dimethyl-4,7-diphenyl-1,10-phenanthrolinato)iridium(III), etc. By way of example, but not limitation, the inorganic material in blue-light emitting material 140 may include silica.

In some embodiments, the inorganic material may be physically bonded to the organic blue-light emitting material to form blue-light emitting material 140. In alternative embodiments, the inorganic material may be covalently bonded to the organic blue-light emitting material to form blue-light emitting material 140. In yet alternative embodiments, the inorganic material may be hydrogen-bonded to a resin (e.g., polyvinylpyrrolidone (PVP) resin) containing the organic blue-light emitting material to form blue-light emitting material 140.

In some embodiments, blue-light emitting material 140 may further include an inorganic shell (e.g., a silica shell) encapsulating the organic blue-light emitting material and the inorganic material.

In some embodiments, blue-light emitting material 140 may have pores on its surface, and the pores may be sealed with a sealant such as a transition metal salt (e.g., a salt of iron, cobalt, nickel, or copper, etc.), a transition metal complex salt (e.g., a complex salt of iron, cobalt, nickel, or copper, etc.), and/or a transition metal chloride (e.g., a chloride of iron, cobalt, nickel, or copper, etc.).

In some embodiments, an LCD backlight or a planar illumination device may utilize transparent light guide 100, which may include a resin 110, red-light emitting material 120, green-light emitting material 130 and blue-light emitting material 140.

As such, by using the hybrid nanoparticle including the organic blue-light emitting material and the inorganic material as blue-light emitting material 140, applying the inorganic shell on the surface of blue-light emitting material 140, and/or sealing the pores of blue-light emitting material 140, it may be possible to reduce or prevent damage against blue-light emitting material 140, which may be caused due to reactive oxygen species generated by excitation of the organic blue-light emitting material. Thus, it may be possible to reduce or prevent the light emitted from transparent light guide 100 from becoming yellowish, thereby attaining uniform luminance and chromaticity in an LCD backlight, or a planar illumination device using transparent light guide 100.

FIGS. 2A-2D schematically show illustrative examples of hybrid nanoparticles 200, 210, 220 and 230, arranged in accordance with at least some embodiments described herein. Hybrid nanoparticles 200, 210, 220 and 230 may be used as blue-light emitting material 140 as described with reference to FIG. 1.

In some embodiments, hybrid nanoparticle 200 as depicted in FIG. 2A may include an organic blue-light emitting material, and an inorganic material bonded to the organic blue-light emitting material. In some embodiments, the organic blue-light emitting material may include at least one of a blue fluorescent material and a blue phosphorescent material. By way of example, but not limitation, the blue fluorescent material may include at least one of 9,10-dibromoanthracene, a bis-(triazinylamino)stilbenedisulfonic acid derivative, a bis-stilbiphenyl derivative, and 2,5-bis(5-tert-butyl-2-benzoxazolyl)thiophene, etc.; and the blue phosphorescent material may include an iridium(III) complex including at least one of tris(2-(2,4-difluorophenyl)pyridinate)iridium(III), bis(2-(2,4-difluorophenyl)pyridinate)picolinic acid iridium(III), tris(3,4,7,8-tetramethyl-1,10-phenantrolinato)iridium(III), and tris(2,9-dimethyl-4,7-diphenyl-1,10-phenanthrolinato)iridium(III), or combination thereof, etc. By way of example, but not limitation, the inorganic material may include silica.

In some embodiments, the inorganic material may be physically bonded to the organic blue-light emitting material to form hybrid nanoparticle 200. In alternative embodiments, the inorganic material may be covalently bonded to the organic blue-light emitting material to form hybrid nanoparticle 200. In yet alternative embodiments, the inorganic material may be hydrogen-bonded to a resin (e.g., polyvinylpyrrolidone (PVP) resin, etc.) containing the organic blue-light emitting material to form hybrid nanoparticle 200.

In some embodiments, in cases where the inorganic material includes silica, hybrid nanoparticle 200 may be formed by dropping a methanol solution of tetramethyl orthosilicate (TMOS) containing the organic blue-light emitting material into a solvent mixture of methanol and water with ammonia catalyst added. In some embodiments, a resin may be added to the methanol solution of tetramethyl orthosilicate (TMOS) containing the organic blue-light emitting material. By way of example, but not limitation, polyvinylpyrrolidone (PVP) resin may be added to the methanol solution of the TMOS containing the organic blue-light emitting material, and the amount of the PVP resin may be about 5% to 20% of the TMOS.

Figure 2B:
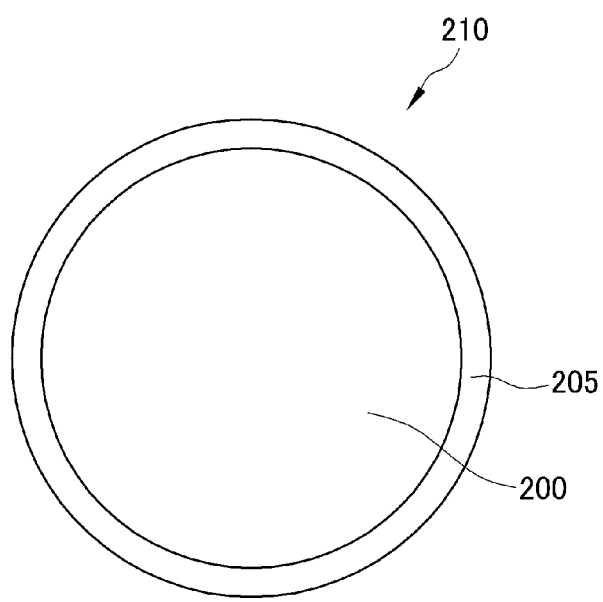

In some embodiments, hybrid nanoparticle 210 as depicted in FIG. 2B may include an inorganic shell 205 encapsulating the organic blue-light emitting material and the inorganic material bonded to each other. That is, hybrid nanoparticle 210 may include inorganic shell 205 in addition to hybrid nanoparticle 200 in FIG. 2A. In some embodiments, inorganic shell 205 may include a silica shell, which may prevent damage due to reactive oxygen species generated by excitation of the organic blue-light emitting material.

By way of example, but not limitation, the particle diameter of hybrid nanoparticle 200 may be in the range between about 20 nm and about 60 nm. Specific examples of the particle diameter may include about 20 nm, about 25 nm, about 30 nm, about 35 nm, about 40 nm, about 45 nm, about 50 nm, about 55 nm, about 60 nm, and ranges between any two of these values (including endpoints). By way of example, but not limitation, the thickness of inorganic shell 205 may be in the range between about 5 nm and about 10 nm. Specific examples of the thickness may include about 5 nm, about 6 nm, about 7 nm, about 8 nm, about 9 nm, about 10 nm, and ranges between any two of these values (including endpoints). By way of example, but not limitation, the volume ratio of hybrid nanoparticle 200 to inorganic shell 205 may be in the range between about 100:60 and about 100:250, depending on the particle diameter of hybrid nanoparticle 200. Specific examples of the volume ratio may include about 100:60, about 100:70, about 100:80, about 100:90, about 100:100, about 100:110, about 100:120, about 100:130, about 100:140, about 100:150, about 100:160, about 100:170, about 100:180, about 100:190, about 100:200, about 100:210, about 100:220, about 100:230, about 100:240, about 100:250, and ranges between any two of these values (including endpoints).

Figure 2C:
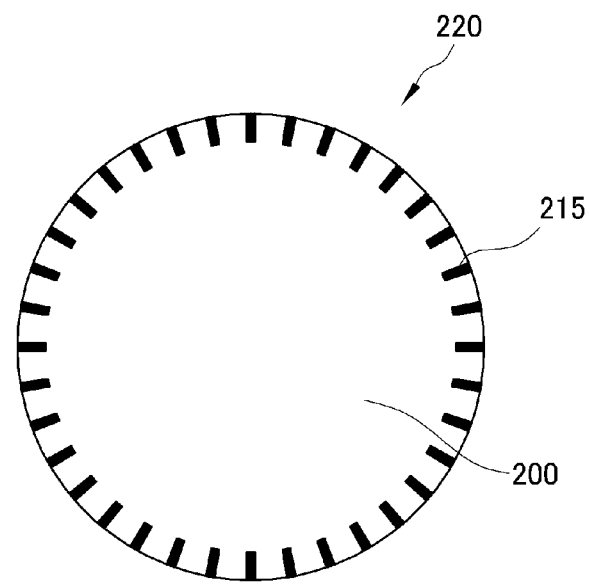

In some embodiments, hybrid nanoparticle 220 as depicted in FIG. 2C may include a sealant 215, which may seal pores on a surface of the organic blue-light emitting material and the inorganic material bonded to each other. That is, hybrid nanoparticle 220 may include sealant 215 in addition to hybrid nanoparticle 200 in FIG. 2A. In some embodiments, sealant 215 may include a transition metal salt, a transition metal complex salt, a transition metal chloride, or combination thereof, etc., and any other material that may prevent damage due to reactive oxygen species generated by excitation of the organic blue-light emitting material, for example, by quenching the reactive oxygen species.

Figure 2D:
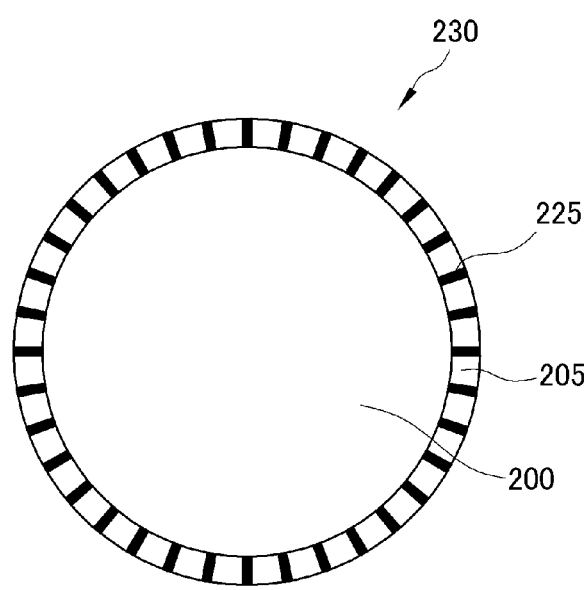

In some embodiments, hybrid nanoparticle 230 as depicted in FIG. 2D may include a sealant 225, which may seal pores on a surface of inorganic shell 205 encapsulating the organic blue-light emitting material and the inorganic material bonded to each other. That is, hybrid nanoparticle 230 may include sealant 225 in addition to hybrid nanoparticle 210 in FIG. 2B. In some embodiments, sealant 225 may include a transition metal salt, a transition metal complex salt, a transition metal chloride, or combination thereof, etc., and any other material that may prevent damage due to reactive oxygen species generated by excitation of the organic blue-light emitting material, for example, by quenching the reactive oxygen species.

FIG. 3 illustrates an example flow diagram of a process 300 for forming a hybrid nanoparticle, arranged in accordance with at least some embodiments described herein.

An example process 300 may include one or more operations, actions, or functions as illustrated by one or more blocks 310, 320, 330 and/or 340. Although illustrated as discrete blocks, various blocks may be divided into additional blocks, combined into fewer blocks, or eliminated, depending on the desired implementation.

At block 310, an organic blue-light emitting material and an inorganic material may be provided. By way of example, but not limitation, the organic blue-light emitting material may include a blue fluorescent material including 9,10-dibromoanthracene, a bis-(triazinylamino)stilbenedisulfonic acid derivative, a bis-stilbiphenyl derivative, and 2,5-bis(5-tert-butyl-2-benzoxazolyl)thiophene, etc.; and/or a blue phosphorescent material including tris(2-(2,4-difluorophenyl)pyridinate)iridium(III), bis(2-(2,4-difluorophenyl)pyridinate)picolinic acid iridium(III), tris(3,4,7,8-tetramethyl-1,10-phenantrolinato)iridium(III), and tris(2,9-dimethyl-4,7-diphenyl-1,10-phenanthrolinato)iridium(III), or combination thereof, etc. By way of example, but not limitation, the inorganic material may include silica.

At block 320, the organic blue-light emitting material and the inorganic material may be bonded to each other. The bonded organic blue-light emitting material and inorganic material may form hybrid nanoparticle 200 as depicted in FIG. 2A.

In some embodiments, the organic blue-light emitting material and the inorganic material may be bonded to each other physically.

In other embodiments, the organic blue-light emitting material and the inorganic material may be covalently bonded to each other by preparing a compound of the organic blue-light emitting material and an alkoxy group, and hydrolysis-condensing the alkoxy group with an alkoxysilane. By way of example, but not limitation, the alkoxy group may be an ethoxy group, and the alkoxysilane may be tetraethoxysilane (TEOS).

In yet other embodiments, the organic blue-light emitting material and the inorganic material may be covalently bonded to each other by pi-electron-conjugating the organic blue-light emitting material and a silane coupling agent containing an alkoxy group, and hydrolysis-condensing the alkoxy group with an alkoxysilane. By way of example, but not limitation, the silane coupling agent may include phenyltriethoxysilane, the alkoxy group may include an ethoxy group, and the alkoxysilane may include tetraethoxysilane (TEOS).

In still yet other embodiments, the organic blue-light emitting material and the inorganic material may be bonded to each other by mixing the organic blue-light emitting material with a resin, and forming a hydrogen-bond between the resin and the inorganic material. By way of example, but not limitation, the resin may include a polyvinylpyrrolidone (PVP) resin.

At block 330, the bonded organic blue-light emitting material and inorganic material may be coated with an inorganic shell. By way of example, but not limitation, the inorganic shell may include a silica shell. The organic blue-light emitting material and the inorganic material bonded with each other and coated with the inorganic shell may form hybrid nanoparticle 210 as depicted in FIG. 2B.

At block 340, pores of the inorganic shell may be sealed with a sealant. By way of example, but not limitation, the sealant may include a transition metal salt, a transition metal complex salt, and a transition metal chloride, or combination thereof, etc. The organic blue-light emitting material and the inorganic material bonded with each other, coated with the inorganic shell and sealed with the sealant may form hybrid nanoparticle 230 as depicted in FIG. 2D.

One skilled in the art will appreciate that, this and other processes and methods disclosed herein may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. For example, between blocks 320 and 330, a step in which the bonded organic blue-light emitting material and inorganic material may be sealed with a sealant (e.g., a transition metal salt, a transition metal complex salt, and a transition metal chloride, etc.) may be added.

EXAMPLES

The present disclosure will be understood more readily by reference to the following examples, which are provided by way of illustration and are not intended to be limiting in any way.

Example 1

Fabrication of Hybrid Nanoparticles

A solvent mixture of 220 grams of methanol and 75 grams of water, with 8 grams of 28% ammonia is prepared. A solution in which 35 grams of tetramethyl orthosilicate (TMOS) and 0.035 grams of an organic blue-light emitting material are dissolved in 45 grams of methanol is also prepared. Then, hybrid nanoparticles with a diameter of 20 nm are provided by dropping the solution into the solvent mixture. When the solvent mixture contains 16 grams of 28% ammonia, the hybrid nanoparticles with a diameter of 60 nm are provided.

3 grams of the hybrid nanoparticles are dispersed in a mixture of 520 grams of water and 80 grams of 28% ammonia. Then, a liquid in which 260 grams of metasilicic acid with 2.0% of $SiO_2$ are dropped into the dispersion is prepared. Then, the liquid is stirred at 80° C. for 3 hours. This provides silica-coated hybrid nanoparticles.

A sealing liquid is prepared by adding 960 ml of water to 40 ml of Top Seal H-298 (produced by Okuno Chemical Industries), which is a nickel acetate-based sealant. The sealing liquid is heated to 90° C. Then, 1 gram of the hybrid nanoparticles are added to the sealing liquid. The mixture of the hybrid nanoparticles and the sealing liquid are stirred for 2 minutes, cooled to room temperature, and then centrifuged at 10,000 rpm for 30 minutes. This provides sealed hybrid nanoparticles.

Example 2

Fabrication of Transparent Light Guides 6.9 grams of a mixture of a red-light emitting material, a green-light emitting material, and a blue-light emitting material, the mixture ratio of which is 15:79:6, is prepared. The mixture of light emitting materials is further mixed with 48 grams of methyl methacrylate and 0.05 grams of benzoyl peroxide. The mixture is then heated to 80° C. to be prepolymerized, and then injected between two glass plates. The edge of the two glass plates is 12 cm, and the distance between the two glass plates is 5 mm. Then, the mixture is left as it is for 15 hours at room temperature, heated in an oven at 55° C. for 3 hours, and then cured in the oven at 45° C. for 12 hours. This provides a transparent light guide uniformly containing the red-light emitting material, the green-light emitting material, and the blue-light emitting material.

JELCON FC-A5 (SSD) (produced by Jujo Chemical Co., Ltd.), which contains titanium oxide fillers, is screen-printed on a surface of the transparent light guide, and then dried. This provides a reflecting sheet covering the surface of the transparent light guide.

Example 3

Performance Improvement Test for Hybrid Nanoparticles and Transparent Light Guides Using Hybrid Nanoparticles Example 3-1

Preparation of Pigment Solution and Treatment Liquids

An acrylic solution colored with Rhodamine B ([9-(2-carboxyphenyl)-6-diethylamino-3-xanthenylidene]-diethylammonium chloride) is prepared as a pigment solution by mixing 0.2 grams of 0.55 wt % Rhodamine B-ethylene glycol solution with 15 grams of 2.5 wt % polymethylmethacrylate (PMMA)-chloroform solution. Rhodamine B is a fluorescent dye, whose absorbance has a peak at approximately 553 nm.

A silica coating liquid having a solid content ratio of 2.5 wt % is prepared by adding 1.18 grams of Methyl Silicate 51 (produced by Colcoat Co., Ltd.) and 0.81 grams of 0.1 N nitric acid to 1.77 grams of ethanol, stirring the mixture for 30 minutes at room temperature, and then adding 20.3 grams of ethanol. Methyl Silicate 51 is a tetramer-in-average composition obtained by hydrolysis-condensing methyl silicate.

A sealing liquid is prepared by adding 96 ml of water to 4 ml of Top Seal H-298 (produced by Okuno Chemical Industries). Top Seal H-298 is a nickel acetate-based sealant that is used when sealing anodic oxide films grown on aluminum or an aluminum alloy.

Example 3-2

Preparation of Samples

The acrylic solution colored with Rhodamine B is applied to a glass substrate by spin coating, and dried in an oven at 80° C. for 30 minutes. This provides an acrylic film colored with Rhodamine B. This acrylic film is used as an untreated sample for comparison (hereinafter, Sample 1).

Further, the silica coating liquid is applied by spin coating to the acrylic film colored with Rhodamine B, which is prepared as above, and dried in an oven at 80° C. for 30 minutes. This provides a silica-coated sample (hereinafter, Sample 2).

Furthermore, the silica-coated sample is immersed for two minutes in the sealing liquid, which has been heated to 90° C., washed with water, and allowed to dry naturally. This provides a silica-coated and sealed sample (hereinafter, Sample 3).

Example 3-3

Light-Resistance Test

Figure 4A:
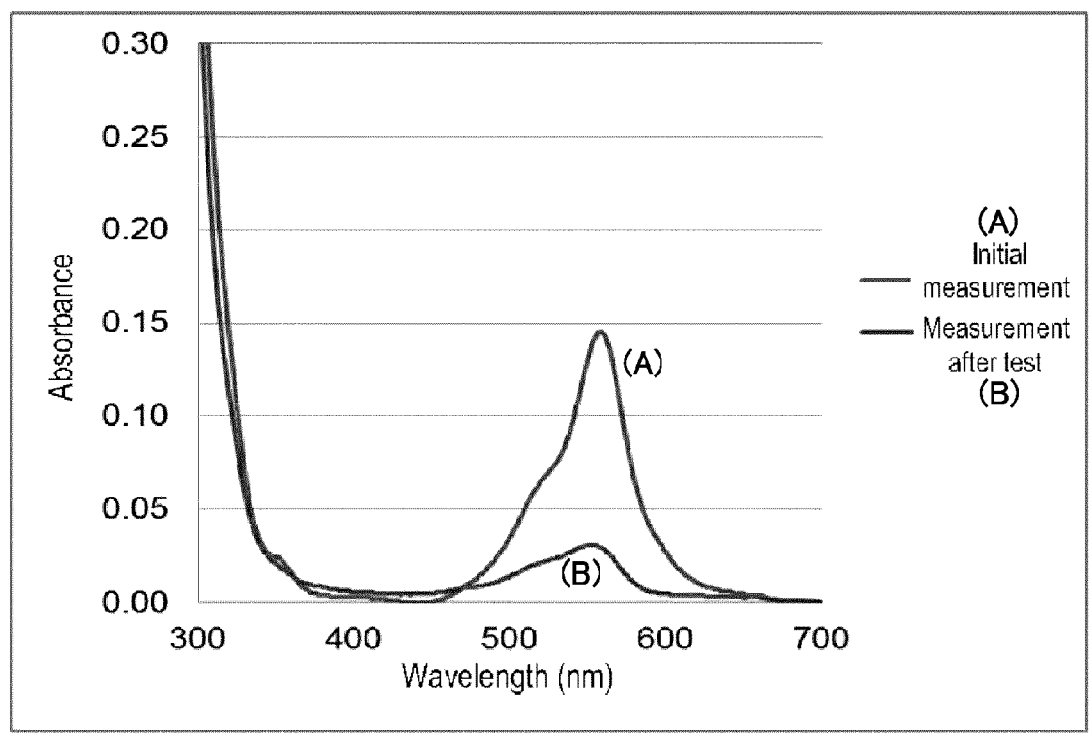
FIGS. 4A-4C illustrate absorption spectra of illustrative examples of hybrid nanoparticles, arranged in accordance with at least some embodiments described herein.
Figure 4B:
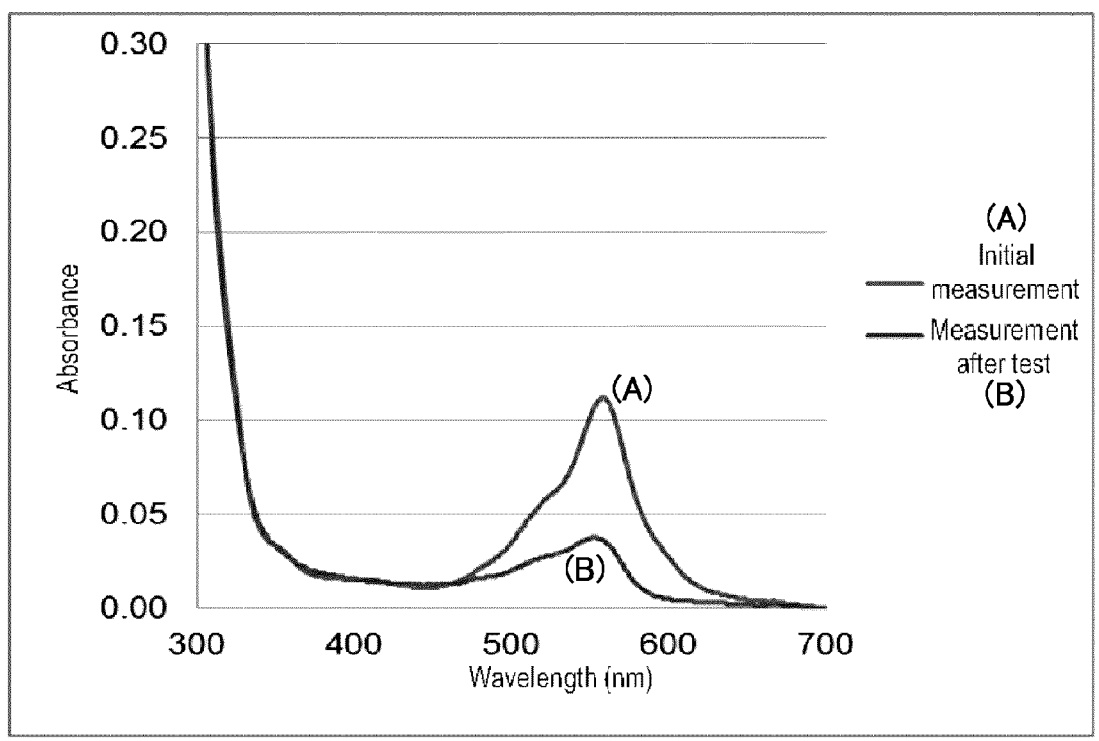
Figure 4C:
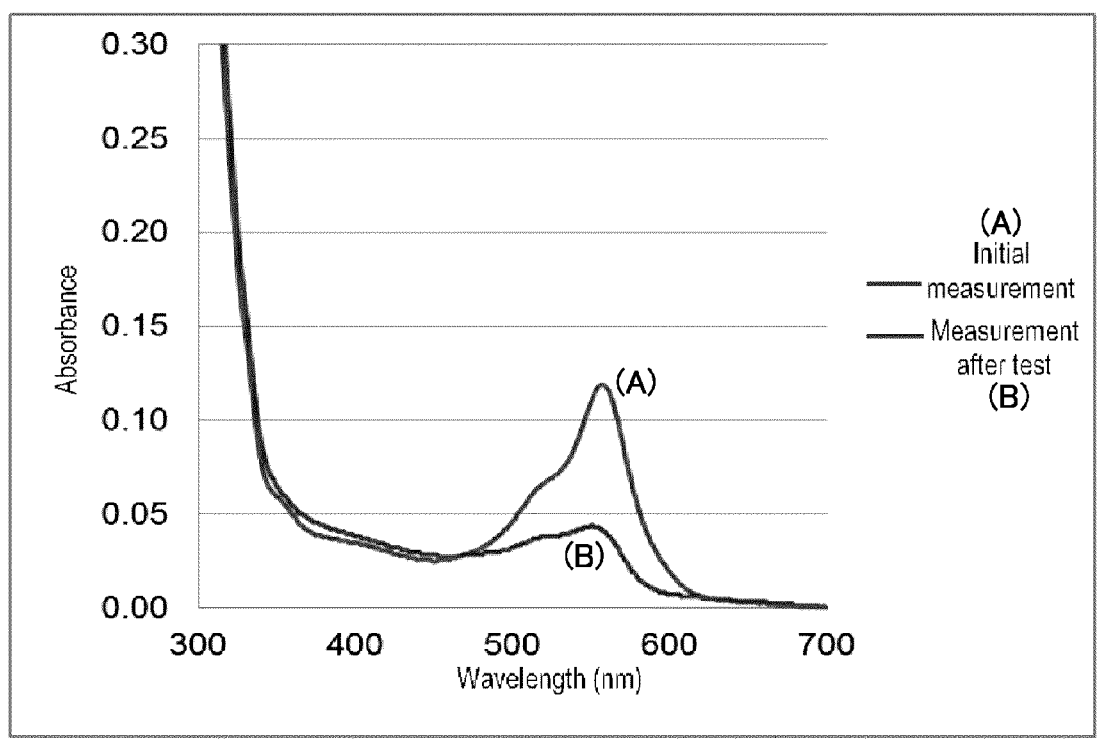

The above three samples are irradiated for five hours using a halogen lamp for the light-resistance test. To measure the light-resistance, initial absorption spectra and post-irradiation absorption spectra of the respective samples are compared. The absorption spectra are measured using a spectrophotometer (UV-3600 manufactured by Shimadzu Corporation). FIGS. 4A-4C respectively show the initial absorption spectra and the post-irradiation absorption spectra of Samples 1-3.

A persistence ratio representing the ratio between the absorbance peak intensities at 553 nm in the post-irradiation absorption spectra and the absorbance peak intensities at 553 nm in the initial absorption spectra is calculated for each of Samples 1-3. The persistence ratio calculated for each of Samples 1-3 is as in Table 1 below.

TABLE 1

| | Sample 1 | Sample 2 | Sample 3 |
|---|---|---|---|
| Persistence Ratio | 21.9% | 35.2% | 37.2% |

As such, improvements in the light-resistance are observed for Sample 2 and Sample 3. That is, improvements in the light-resistance due to silica-coating and sealing are observed.

Example 3-4

Luminance and Chromaticity Test

Figure 5A:
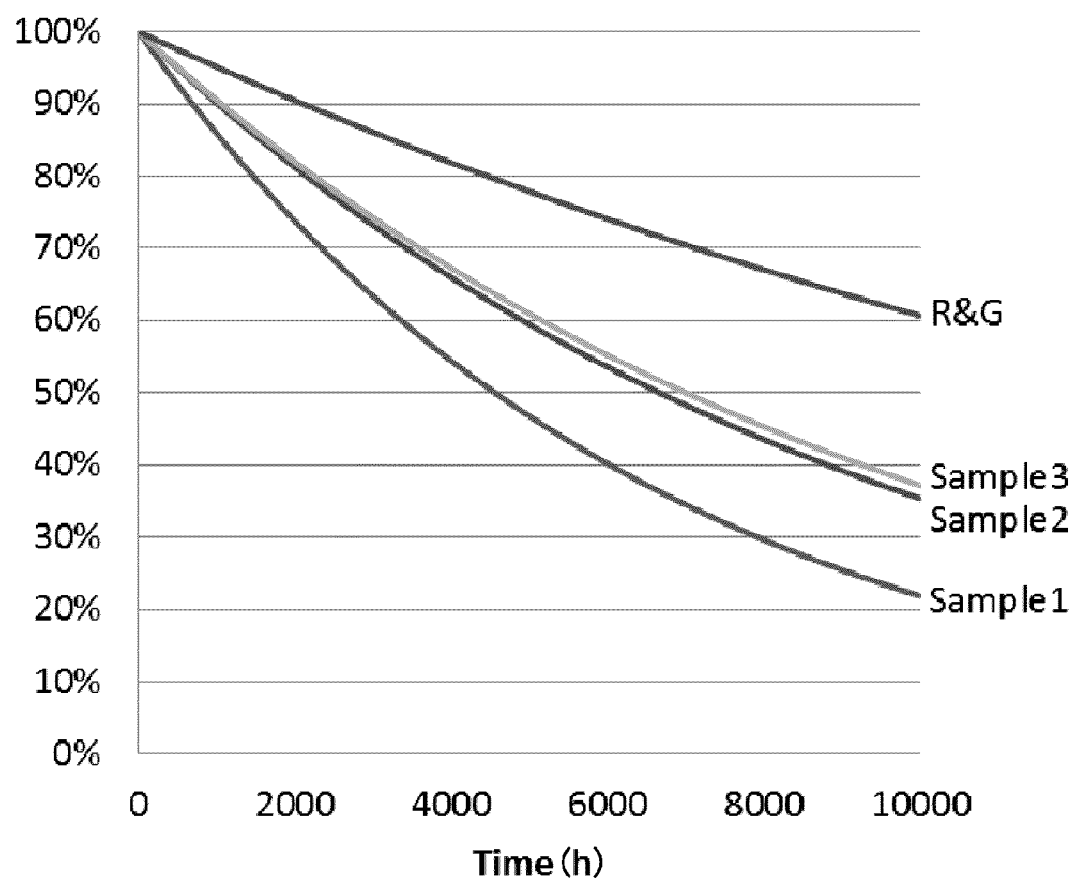
FIG. 5A shows changes of persistence ratios of illustrative examples of hybrid nanoparticles, arranged in accordance with at least some embodiments described herein.

Assuming that the above persistence ratios of three samples (21.9% of Sample 1, 35.2% of Sample 2, and 37.2% of Sample 3) are obtained after 10,000 hours of operation, the persistence ratio of red and green light emitting materials is 95.0% after 1,000 hours of operation, and the persistence ratios exponentially decrease, the persistence ratios for each of Samples 1-3 and red and green light emitting materials after 1,000 hours and after 5,000 hours of operation are calculated as in Table 2 below. FIG. 5A shows the changes of the persistence ratios for Samples 1-3 and red and green light emitting materials ("R&G") for 10,000 hours.

TABLE 2

| Time of Operation | Sample 1 | Sample 2 | Sample 3 | Red & Green |
|---|---|---|---|---|
| 1,000 hours | 85.9% | 90.1% | 90.6% | 95.0% |
| 5,000 hours | 46.8% | 59.5% | 61.0% | 77.9% |

Figure 5B:
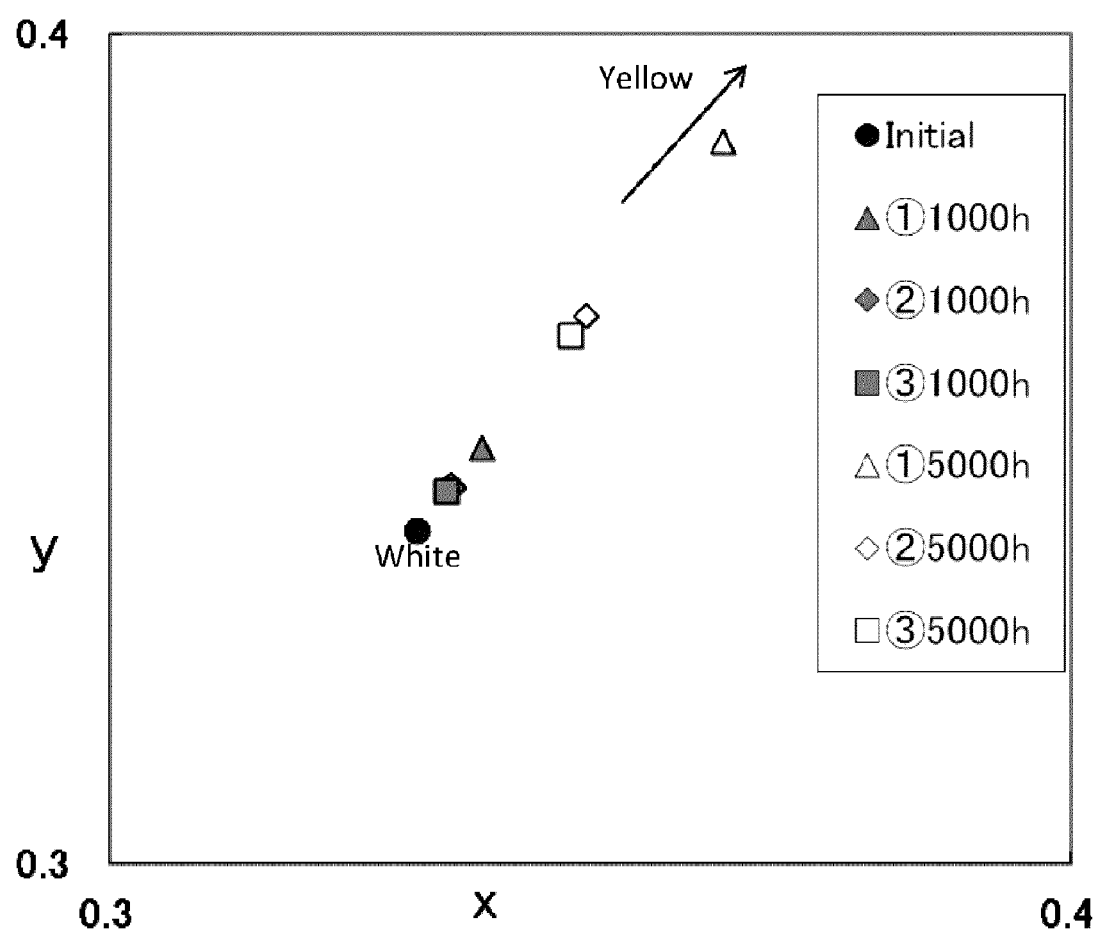
FIG. 5B shows changes of chromaticity of illustrative examples of transparent light guides, arranged in accordance with at least some embodiments described herein.

In such cases, the change of luminance and chromaticity of a transparent light guide containing each of Samples 1-3 is as in Table 3 below. FIG. 5B shows the change of chromaticity of the transparent light guide containing each of Samples 1-3.

TABLE 3

| Time of Operation | Sample No. | Change of Luminance | Chromaticity x | Chromaticity y |
|---|---|---|---|---|
| Initial | Samples 1-3 | 100.0% | 0.3320 | 0.3400 |
| 1,000 hours | Sample 1 | 94.3% | 0.3387 | 0.3499 |
|  | Sample 2 | 94.6% | 0.3355 | 0.3452 |
|  | Sample 3 | 94.7% | 0.3352 | 0.3447 |
| 5,000 hours | Sample 1 | 75.5% | 0.3638 | 0.3870 |
|  | Sample 2 | 76.5% | 0.3496 | 0.3659 |
|  | Sample 3 | 76.6% | 0.3480 | 0.3636 |

As such, improvements in the luminance and chromaticity are observed for Sample 2 and Sample 3. That is, improvements in the luminance and chromaticity due to silica-coating and sealing are observed.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A hybrid nanoparticle comprising:
   an organic blue-light emitting material; and
   an inorganic material bonded to the organic blue-light emitting material;
   wherein the hybrid nanoparticle further comprises an inorganic shell encapsulating the organic blue-light emitting material and the inorganic material, and
   wherein pores of the inorganic shell are sealed with at least one of a transition metal salt, a transition metal complex salt, and a transition metal chloride.

2. The hybrid nanoparticle of claim 1, wherein the organic blue-light emitting material comprises at least one of a blue fluorescent material and a blue phosphorescent material.

3. The hybrid nanoparticle of claim 2, wherein the blue fluorescent material comprises at least one of 9,10-dibromoanthracene, a bis-triazinylamino)stil benedisulfonic acid derivative, a bis-stilbiphenyl derivative, and 2,5-bis(5-tert-butyl-2-benzoxazolyl)thiophene, and wherein the blue phosphorescent material comprises an iridium(III) complex including at least one of tris(2-(2,4-difluorophenyl)pyridinate) iridium(III), bis(2-(2,4-difluorophenyl) pyridinate)picolinic acid iridium (III), tris(3,4,7,8-tetramethyl-1,10-phenantronato) iridium(III), and tris(2,9-dimethyl-4,7-diphenyl-1,10-phenanthrolinato) iridium(III).

4. The hybrid nanoparticle of claim 1, where the inorganic material comprises silica.

5. The hybrid nanoparticle of claim 1, wherein the inorganic material is physically bonded to the organic blue-light emitting material, covalently bonded to the organic blue-light emitting material, or hydrogen-bonded to a resin containing the organic blue-light emitting material.

6. The hybrid nanoparticle of claim 1, wherein the inorganic shell comprises a silica shell.

7. A transparent light guide comprising:
   a resin containing at least one red-light emitting material, at least one green-light emitting material, and at least one organic blue-light emitting material bonded with an inorganic material, wherein the resin comprises an acrylic resin; and
   a reflecting sheet;
   wherein a surface of the at least one organic blue-fight emitting material bonded with the inorganic material is sealed with at least one of a transition metal salt, a transition metal complex salt, and a transition metal chloride,
   and further wherein the reflecting sheet is disposed to cover a surface of the resin.

8. The transparent light guide of claim 7, wherein the at least one red-light emitting material comprises a $Eu^{3+}$ tri-n-butyl complex.

9. The transparent light guide of claim 7, wherein the at least one green-light emitting material comprises a $Tb^{3+}$ tri-n-butyl complex.

10. The transparent light guide of claim 7, wherein the at least one organic blue-light emitting material comprises at least one of a blue fluorescent material including 9,10-dibromoanthracene, a bis-(triazinylamino)stilbenedisulfonic acid derivative, a bis-stilbiphenyl derivative, and 2,5-bis(5-tert-butyl-2-benzoxazolyl)thiophene; and a blue phosphorescent material including tris(2-(2,4-difluorophenyl)pyridinate) iridium(III), bis(2-(2,4-difluorophenyl) pyridinate) picolinic acid iridium(III), tris(3,4,7,8-tetramethyl-1,10-phenantrolinato)iridium(III), and tris(2,9-dimethyl-4,7-diphenyl-1,10-phenanthrolinato) iridium(III).

11. The transparent light guide of claim 7, wherein the inorganic material comprises silica and the at least one organic blue-light emitting material bonded with the inorganic material is coated with the silica.

12. A backlight for a liquid crystal display comprising the transparent light guide of claim 7.

13. A planar illumination device comprising the transparent light guide of claim 7.

14. A method of forming a hybrid nanoparticle, the method comprising:
   providing an organic blue-light emitting material; and
   bonding an inorganic material to the organic blue-light emitting material to form the hybrid nanoparticle;
   wherein the method further comprises encapsulating the organic blue-light emitting material and the inorganic material bonded to each other in an inorganic shell, and sealing pores of the inorganic shell with at least one of a transition metal salt, a transition metal complex salt, and a transition metal chloride.

15. The method of claim 14, wherein the organic blue-light emitting material comprises at least one of a blue fluorescent material including at least one of 9,10-dibromoarithracene, a bis-(triazinylamino)stilbenedisulfonic acid derivative, a bis-stilbiphenyl derivative, and 2,5-bis(5-tert-butyl-2-benzoxazolyl)thiophene; and a blue phosphorescent material including at least one of tris(2-(2,4-difluorophenyl) pyridinate) iridium(III), bis(2-(2,4-difluorophenyl) pyridinate)picolinic acid iridium(III), tris(3,4,7,8-tetramethyl-1, 10-phenantrolinato) iridium(III), and tris(2,9-dimethyl-4,7-diphenyl-1,10-phenanthrolinato) iridium(III).

16. The method of claim 14, wherein the inorganic material comprises silica and wherein the bonding comprises bonding the inorganic material to the organic blue-light emitting material physically.

17. The method of claim 14, wherein the bonding step comprises:
   preparing a compound of the organic blue-light emitting material and an alkoxy group; and
   hydrolysis-condensing the alkoxy group with an aikoxysilane, wherein the alkoxy group is an ethoxy group, and the alkoxysilane is tetraethoxysilane (TEOS).

18. The method of claim 14, wherein the bonding step comprises:
   pi-electron-conjugating the organic blue-light emitting material and a silane coupling agent containing an alkoxy group, wherein the silane coupling agent comprises phenyltriethoxysilane, the alkoxy group comprises an ethoxy group, and the alkoxysilane comprises tetraethoxysilane (TEOS); and hydrolysis-condensing the alkoxy group with an alkoxysilane.

19. The method of claim 14, wherein the bonding step comprises:

mixing the organic blue-light emitting material with a resin; and forming a hydrogen-bond between the resin and the inorganic material.

20. The method of claim 14, wherein the hybrid nanoparticle has pores, and wherein the method further comprises:

sealing the pores of the hybrid nanoparticle with at least one of a transition metal salt, a transition metal complex salt, and a transition metal chloride.

* * * * *

UNITED STATES PATENT AND TRADEMARK OFFICE
CERTIFICATE OF CORRECTION

PATENT NO. : 9,759,855 B2
APPLICATION NO. : 14/769285
DATED : September 12, 2017
INVENTOR(S) : Hayama It is certified that error appears in the above-identified patent and that said Letters Patent is hereby corrected as shown below:

In the Claims

In Column 13, Line 36, in Claim 3, delete "nanoparticie" and insert -- nanoparticle --, therefor.

In Column 13, Line 38, in Claim 3, delete "bis-triazinylamino)stil benedisulfonic" and insert -- bis-(triazinylamino)stilbenedisulfonic --, therefor.

In Column 13, Line 63, in Claim 7, delete "blue-fight" and insert -- blue-light --, therefor.

In Column 14, Lines 42-43, in Claim 15, delete "10-dibromoarithracene," and insert -- 10-dibromoanthracene, --, therefor.

In Column 14, Lines 59-60, in Claim 17, delete "an aikoxysilane," and insert -- an alkoxysilane, --, therefor.

Signed and Sealed this
Thirty-first Day of July, 2018

Andrei Iancu
*Director of the United States Patent and Trademark Office*